United States Patent [19]

McKenney et al.

[11] Patent Number: 5,357,640
[45] Date of Patent: Oct. 25, 1994

[54] DRESSING-AID-AND-TRANSFER DEVICE

[75] Inventors: Michael A. McKenney, Gardiner; Daniel McKenney, Augusta, both of Me.

[73] Assignee: McKenney Group, Portland, Me.

[21] Appl. No.: 155,571

[22] Filed: Nov. 16, 1993

Related U.S. Application Data

[63] Continuation-in-part of Ser. No. 50,503, Apr. 20, 1993, abandoned.

[51] Int. Cl.$^5$ .......................... A61G 7/10; A61G 7/14
[52] U.S. Cl. ........................................................ 5/81.1
[58] Field of Search ........................ 5/81.1, 86.1, 83.1

[56] References Cited

U.S. PATENT DOCUMENTS

| | | | |
|---|---|---|---|
| 4,279,043 | 7/1981 | Saunders | 5/81.1 |
| 4,435,863 | 3/1984 | Lerich | 5/81.1 |
| 4,510,633 | 4/1985 | Thorne | 5/81.1 |
| 4,843,661 | 7/1989 | Skihinski | 5/81.1 |
| 4,934,003 | 6/1990 | Hayakawa et al. | 5/81.1 |
| 4,969,221 | 11/1990 | Foster | 5/81.1 |
| 5,093,944 | 3/1992 | Winston, Sr. | 5/81.1 |
| 5,189,741 | 3/1993 | Beardmore | 5/81.1 |

FOREIGN PATENT DOCUMENTS 2526312 11/1983 France ..................... 5/81.1

Primary Examiner—Alexander Grosz
Attorney, Agent, or Firm—Chris A. Caseiro; Thomas L. Bohan

[57] ABSTRACT

A dressing-aid-and-transfer device for assisting attendants and patients in moving and dressing. The device includes a space frame with support legs of the space frame defining a device perimeter. A chest support is provided to support the weight of the patient being moved. The space frame is designed so as to provide a stable and lightweight transferral device that is transportable and easy for a single person to operate. The support legs and reinforcing cross-pieces are configured to provide structurally stability without interfering with an attendant's ability to easily remove and place clothing on a patient's lower body. The support legs pivot at the base of the space frame in order to reduce the force required to transfer a patient to and from a sitting position. Optional features include a rotatable base and the use of actuators to reduce the effort required to tilt the space frame.

26 Claims, 4 Drawing Sheets

DRESSING-AID-AND-TRANSFER DEVICE

This is a continuation-in-part of application Ser. No. 050,503, filed Apr. 20, 1993, now abandoned.

BACKGROUND OF THE INVENTION

1. Field of the invention

This invention relates to a device that can be used to reduce the difficulty in dressing and transferring disabled and/or incapacitated people. In particular, the present invention relates to a device that permits those attending disabled or incapacitated people to easily move, dress and conduct hygienic cleaning of the disabled or incapacitated person. More particularly, the present invention is a device used to move such a person from a sitting position and to orient that person so that, at most, only one attendant is needed to conduct the move, dressing, and/or cleaning.

2. Description of Prior Art.

Attending to a disabled or incapacitated person, hereafter referred to as a "patient," has long been a labor-intensive and difficult task. Because such patients are not capable of standing or walking by themselves they require assistance while dressing, moving to a wheel chair, getting up from a chair, a seat or a bed and using the bathroom. Because patients often have little strength to move themselves, those assisting them must bear a substantial portion and sometimes the full body weight of the patient to complete the task at hand. Often, moving the full weight of a patient is impossible for a single attendant to safely accomplish. Hence, attendants and patients need a device that assists them in their needs.

Conventional technology to lift or transfer patients often employs complex hoist mechanisms that use sling-like members to hold patients. These devices are complex, often employing hydraulic, electrical and mechanical systems that are costly. Typically, such devices permitting the move to be conducted by a single attendant are stationary devices, or at least very difficult to move from one location to another. Further, they are usually impractical, or too costly, to install outside institutions like hospitals and nursing homes. This is particularly troubling for those patients who are cared for at home by spouses, relatives, and other attendants, where use of an easily-transportable transferring device would be particularly helpful.

Attempts have been made to provide simple, less-costly patient-transferring devices. However, these devices have not met the need for a truly easy-to-use, inexpensive, and mobile transferring device that assists attendants in accomplishing the tasks faced when caring for patients.

One example of such a device is disclosed by Hayakawa et al. in U.S. Pat. No. 4,934,003. Hayakawa describes a transfer device having a base assembly, an actuation lever assembly, and a single pivotal support shaft. A saddle is mounted on one end of the support shaft. This assembly-the pivotal support shaft and saddle-is used to support the patient during the transfer. Since the device employs a single support shaft, very high-strength-and, consequently, heavy and expensive materials-must be used in its construction, so as to provide the strength necessary to support the weight of the patient and to ensure stability of the apparatus while the patient is being moved or turned.

Another example of a transferring or transporting device is disclosed by Lerich (U.S. Pat. No. 4,435,863). Lerich describes a device having a base with a support projecting upwardly therefrom, a chest pad, and a linkage assembly coupling the chest pad and the support. The base of the device is mounted on wheels. Uke Hayakawa, the Lerich device employs one support to bear the weight of the patient while the patient is being lifted from a seated position. Further, the Lerich support is located to one side of the device. Since the device employs a side-mounted single-support-shaft design, very high-strength, heavy, and expensive materials must be used in its construction to provide the strength to support the weight of the patient and to provide stability of the apparatus while the patient is being moved.

The prior devices have additional drawbacks. Even when made of strong and expensive materials, they are inherently unstable and therefore potentially unsafe. The support mechanisms of the prior art rely on single shafts which are apt to cause the device to tip on its side under any non-symmetrical loading, thus throwing the patient off. Further, the prior devices noted offer little or no structure upon which patient guides, handles, or holding devices may be attached. An improved device would ensure that patients would be guided to the center of the device so as to lessen the possibility of the device tipping to one side.

In addition, the prior transfer devices fall to provide the capability for self use. Such capability is particularly important when patients live at home and when they have a limited capacity to move. A device that significantly reduces the force required by the individual conducting the transfer to move the patient from a sitting position to a position on the device is thus required. That reduction in required force can be provided by the design of the device itself, or by an automated actuation mechanism acting either in conjunction with the individual's effort or as a stand-alone operational feature. In this way, some patients may be able to eliminate or significantly decrease the need for assistance from attendants, thus reducing the time attendants need to spend with patients (and the consequent expenses) while at the same time regaining a sense of independence.

Prior devices that provide more stable support, such as the systems described by Winston (U.S. Pat. No. 5,093,944) and Thorne (U.S. Pat. No. 4,510,633), also fall to provide structures convenient for dressing patients. In particular, there are often leg or trunk support means that make a single attendant's task of removing and putting on pants, for example, extremely difficult. Further, neither system noted enables a less-than-totally incapacitated patient to operate the device alone.

A more effective transferring device would provide a stable and lightweight support mechanism so as to ensure patient safety and comfort. Such a support mechanism would provide a structure that ensured equal distribution of the patient load so as to minimize the possibility of the device tipping over. The support mechanism would also provide means to reliably guide a patient on to the device as well as easy means for an attendant to do that guiding. Further, such a device would be designed so as to provide effective access to the patient's lower body in order to ease the job of dressing that patient. Still further, an effective transfer device would be inexpensive and portable so that the device could be used in the home and also transported with the patient in his or her travels away from the home. Additionally, an improved and effective device would permit the patient to use it without the assistance of an attendant. The prior-art transferring devices have failed to employ such features. Therefore, there is a need for a lightweight and inexpensive device employing such features, a device that is stable, strong and portable.

SUMMARY OF THE INVENTION

It is an object of the present invention to provide a patient dressing-aid-and-transfer device. It is a further object of the present invention to provide a stable and lightweight patient support mechanism that ensures patient safety and comfort. It is still another object of the present invention to provide such a device that is stable and that retains the patient in a stable manner while permitting access to the patient's lower body. It is yet another object of the present invention to provide a patient dressing-aid-and-transfer device that is portable and inexpensive. Further, it is an object of the invention to provide a transfer-and-dressing aid by which a patient can be lifted from a sitting position not on the device to a position on the device through the use of minimal applied force.

The objects described above are achieved through the present invention, which is a dressing-aid-and-transfer device having a component which can be described as a space frame. The space frame has a plurality of support legs and a plurality of cross-pieces connecting those support legs. The support legs of the space frame form the perimeter of the device, providing enhanced stability because the load on the device is more evenly distributed. The cross-pieces are positioned out of the way of the patient's lower body, with its support legs spaced sufficiently apart so that an attendant has easy access to the lower body for dressing and cleaning purposes. The frames' support legs and cross-pieces are fabricated of strong, lightweight material of sufficient strength to support the full weight of any person. Aluminum tubing has been found to be particularly useful in this regard. Optionally, the support legs are designed to be variable in length so that patients of differing height may employ a single device. The variable length of the support legs may be achieved by having a first set of support-leg tubes inserted into a corresponding second set of support-leg tubes, each with well-known locking means to secure the pairs of leg tubes together when the device is in use. A plurality of locking locations provides a corresponding plurality of device heights. A chest support is placed on, and secured to, the upper portion of the frame, and is preferably attached to all of the frame legs. The chest support must be wide enough and long enough to comfortably and support the patient with sufficient stability.

At least two of the support legs have means that enable the user to pivot the frame on those support legs so that the entire device, not just a section of it, can be cantilevered. In operation, the support legs positioned closest to the patient have pivot mechanisms designed so that the attendant or the patient can swing the frame and chest support toward the sitting patient without concern that those support legs will "kick out" when the patient is placed on the chest support. This can be achieved in a number of well-known ways, including the use of rockers as portions of these "fixed" support legs, or the use of non-skid materials applied between the ground and the bottom of the legs. Of course, the dimensions of the fixed support legs will determine their stability as well-legs with only point contact being less desirable than support legs with a broad base, for example.

While the fixed support legs located nearest the patient remain on the ground, the "unfixed" support legs farthest from the patient are free to move away from the ground (or base) so that the device can be tilted. In this configuration the frame is tilted toward the sitting patient so that he or she may be easily placed on the chest support. After the patient is positioned on the chest support, an attendant, or a patient with some strength and mobility, can force the free-standing support legs back onto the ground or base, thereby raising the patient out of the sitting position. Unlike many prior transfer devices, the present invention is designed to be in a tilted (or metastable) position only during the time the patient is being transferred from the external sitting position to the device. Once the patient is on the device, the device is rotated to its most stable orientation-with all support legs on the ground (or base).

It is a key feature of the present invention that pivoting of the frame about the fixed support legs occurs at the "bottom" region of those support legs, rather than at some point closer to the patient's center of mass. At that lowest possible position the effective lever arm about the fixed point of those support legs is maximized, thereby reducing the force required to draw the patient out of the sitting position and onto the chest support. As a result, even a small attendant can transfer a large patient, and a patient with even a little strength can transfer himself or herself.

Further features of the space frame of the present invention include the incorporation of handles into the upper portion of the frame. The handles can be grasped by the patient or attendant during the transfer. In addition, the handles are preferably designed to act as guides during the placement of the patient on the chest support. They also act as lateral supports to prevent the patient from rolling off the chest support during any type of movement. Of course, supplemental securing means, such as a strap can be deployed on the chest support to enhance the security of the combination of a suitable chest support and the guides/handles.

An optional feature of the transfer device of the present invention includes a rotatable base. The rotatable base is designed to permit the attendant or the patient to rotate the patient away from the chair, bed, etc., on which the patient is initially seated. In this way, transfer, cleaning, and dressing functions can be performed more easily. In order to maintain the stability of the device, it is necessary to have a rotatable base which is stable. That is, the rotatable base must be designed so that, among other things, it will not slide when the patient is being placed on the chest support. This may be achieved by having, in effect, a "lazy susan" type of base whereby the support legs rest on a first base platform which is permitted to rotate on a second base platform. It is not necessary to secure the second base platform to the floor or the ground; however, that second base platform cannot be permitted to slide accidently under any weight shift. Of course, with the lazy susan design the mobility of the present transfer device is limited. Therefore, it is also an option to provide a base with wheels, provided those wheels have suitable, easy-to-operate locking mechanisms.

With the optional base the fixed support legs used as the pivot points for the frame must be attached properly so as to insure adequate safety while still providing the desired cantilever effect. This may be done by hinging the pivoting support legs on the base so that they are firmly secured to the stable base while still free to pivot at the hinge. Of course, the support legs designed to be farthest from the sitting patient are allowed to rest freely on the base. In order to enhance the options available to the patient, the rotatable base may be provided with leg guides into which the fixed support legs may be inserted. In this way, the frame having the support legs and the chest support may be easily detached from the rotatable base. Of course, with this design, the leg guides would have to be hinged, or otherwise designed to swing on the base, in order to provide the necessary pivoting of the fixed support legs when the frame is tilted.

A final optional aspect of the transfer device of the present invention is the use of pneumatic or hydraulic means and a control mechanism to permit the attendant or the patient to control the pivoting of the device with little or no physical effort. Well-known, commercially available actuators are considered to be suitable for the task.

These and other features, aspects, and advantages of the present invention will become better understood with reference to the following description, the drawings, and the appended claims.

BRIEF DESCRIPTION OF THE DRAWINGS

The invention is illustrated in the accompanying drawings.

DETAILED DESCRIPTION OF PREFERRED EMBODIMENTS

Figure 1:
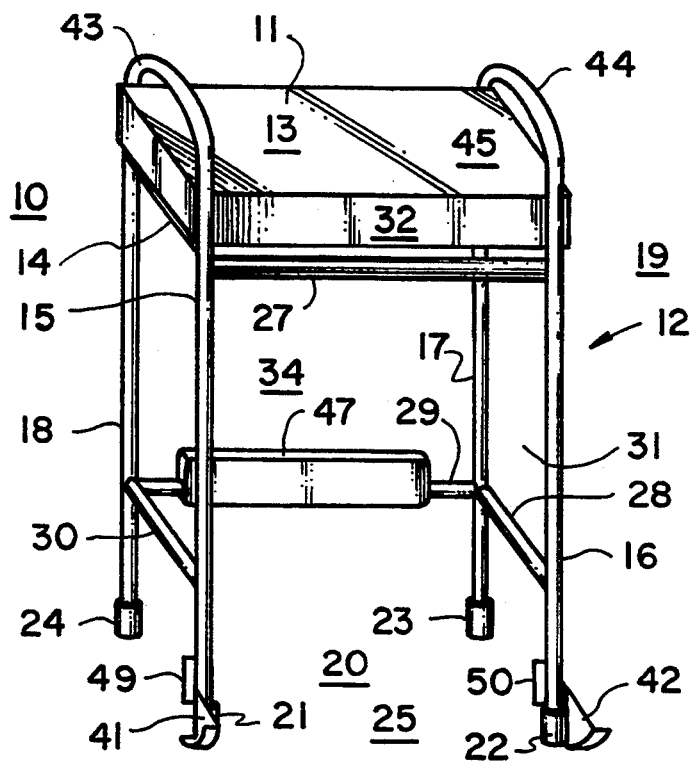
FIG. 1 is a simplified perspective view of the front of the transfer device of the present invention.

As illustrated in the FIGS., a first dressing-aid-and-transfer device 10 of the present invention includes a horizontally-oriented chest support 11 and a space frame 12. The chest support 11 is preferably made with padding 13 suitable to ensure the comfort of a patient resting thereon. A material such as foam rubber, with a covering, has been found to be particularly useful. In the preferred embodiment of the present invention the padding may be secured to an underlying padding support 14, such as a wooden board or a thin aluminum plate, that is in turn used to secure the chest support 11 to the space frame 12. Those skilled in the art can select from a number of suitable materials for the padding 13 and the padding support 14, provided such selections are made based on providing patient comfort and minimal weight to the dressing-aid-and-transfer device 10.

A key feature of the present invention is the design of the space frame 12. As illustrated in the FIGS. 1–3, the space frame 12 is designed to provide stable support for a patient resting on the chest support 11 while at the same time providing an attendant with easy access to that patient's lower body. This is achieved by providing a plurality of vertically-oriented support legs 15–18 that form a support perimeter of the dressing-aid-and-transfer device 10. In keeping with the goal of making a lightweight, stable dressing-aid-and-transfer device 10, the support legs are made of Aluminum tubing with walls thick enough to easily support patient's of any possible weight. It is to be understood that alternative materials could be used with suitable results and that a different number of support legs may be utilized without deviating from the stated goals.

At an upper device region 19, the support legs 15–18 are attached to the chest support 11 via the padding support 14. This may be accomplished in any number of well-known ways, including the use of commercially-available nuts and bolts. At a lower device region 20, each of the support legs 15–18 has corresponding support feet 21–24, all of which rest on a substrate 25. The support feet 21–24 may simply be the bottoms of the support legs 15–18; however, it is preferred that they have a larger cross-sectional area than the support legs 15–18 in order to provide greater stability to the space frame 12. Further, the support feet 21–24 may be made of a material other than that used in the fabrication of the support legs 15–18, a material that preferably has nonskid characteristics. Soft rubber bushings, for example, have been found to be particularly useful in that regard.

in the preferred embodiment of the present invention illustrated in the FIGS., the support legs 15–18, with the chest support 11 and the substrate 25, form a trapezoidal box 26. The trapezoidal box 26 is further characterized by a plurality of support leg cross-pieces 27–30. The cross-pieces 27–30 are connected to the support legs 15–18 in a manner that provides structural reinforcement without interfering in the dressing and cleaning of the patient's lower body. This is achieved in the present invention by positioning the cross-pieces 27–30 around the space frame perimeter formed by the support legs 15–18 so that none of the cross-pieces 27–30 will contact the patient's legs when that patient is resting on the chest support 11. While four cross-pieces 27–30 are illustrated, it is to be understood that more or less can be used, provided structural reinforcement and light weight are maintained.

As illustrated in the FIGS., a front space frame region 31 is formed by a chest support front 32, the substrate 25, and support legs 15 and 16. It is via this front space frame region 31 that the patient's legs enter the trapezoidal box 26 formed by the space frame 12 when the patient is first transferred from a sitting position to one of being prone on the chest support 11. Therefore, a front cross-piece 27, connecting and reinforcing support legs 15 and 16, must be located at the upper device region 19 sufficiently close to the chest support 11 that the patient's legs will not be blocked from entering the trapezoidal box 26. Preferably, that front cross-piece 27 must also be horizontally oriented. Placing the front cross-piece 27 in this way further permits an attendant to remove the patient's lower-body clothing without any interference. The remaining cross-pieces 28–30, are located on a first side space frame region 33, a back space frame region 34, and a second side space frame region 35, respectively. First side cross-piece 28 connects together and reinforces support legs 16 and 17, back cross-piece 29 connects together and reinforces support legs 17 and 18, and second side cross-piece 30 connects together and reinforces support legs 15 and 18. While illustrated as being horizontally oriented, it is to be understood that cross-pieces 28–30 may alternatively be placed diagonally, as required. All cross-pieces 27–30 may be fabricated of suitable, lightweight and strong material, including the same type of Aluminum tubing used to make the support legs 15–18. Further, the cross-pieces 27–30 are affixed to the support legs 15–18 using well-known means, including nuts and bolts or welding.

Figure 4:
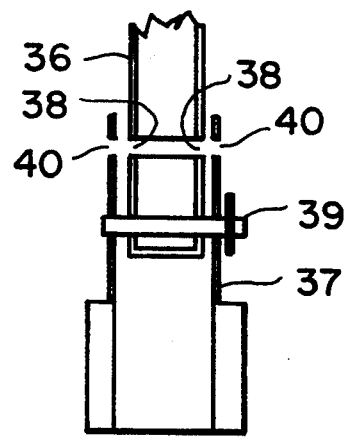
FIG. 4 is a simplified side elevation view of an exemplar optional telescoping support leg design of the present invention.

It is contemplated in the present invention that the dressing-aid-and-transfer device 10 may be used by patients of different heights. Since the present invention is designed primarily to easily transfer a patient from a sitting position, there is a need for only a few different height levels of the space frame 12. Therefore, an optional feature of the present invention is to make each of the support legs 15–18 in two sections. FIG. 4 illustrates an exemplar support leg made of two sections, an upper support leg section 36 and a lower support leg section 37. As illustrated, the lower support leg section 37 is slightly larger than the upper support leg section 36 so that the upper support leg section 36 fits into the lower support leg section 37. Any one of a plurality of upper height-change holes 38 in the upper support section 36 permit the user to insert a locking pin 39 therein when any one of the upper height-change holes 38 is matched with any one of a plurality of lower height-change holes 40 in the lower support leg section 37. Of course, it is preferable that each of the support legs 15–18 is designed similarly. In this way, the height of the dressing-aid-and-transfer device 10 may be raised or lowered-and secured-as desired. Preferably, a nominal device height of 30" is contemplated. It is to be understood, that the same result can be achieved by including, but not limiting to, designs where the upper support leg section 36 is made larger than the lower support leg section 37, and where the chest support 11 is provided with an actuator or spring mechanism so that it alone may be raised and lowered.

Figure 2:
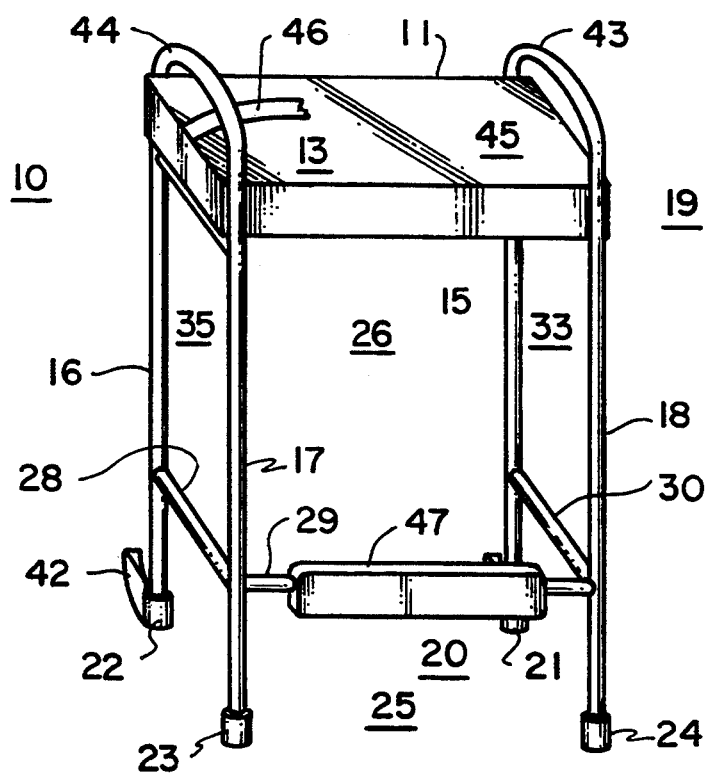
FIG. 2 is a simplified perspective view of the rear of the transfer device of the present invention.
Figure 3:
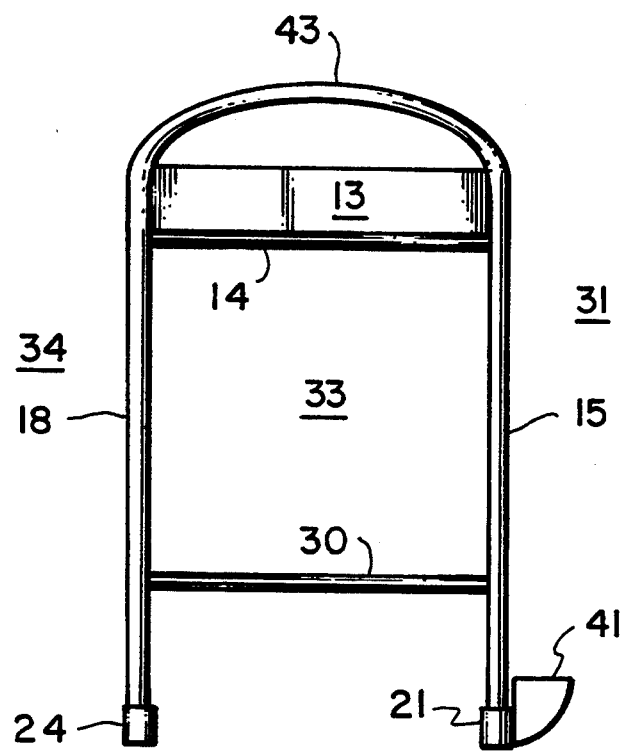
FIG. 3 is a simplified side elevation view of the transfer device of the present invention, showing the optional supplemental handles.

A key feature of the present invention is the provision for pivoting the space frame 12 toward a sitting patient while still providing for stability of the device throughout the transfer of the patient from the seated to the prone position on the chest support 11. This is achieved by supplementing support feet 21 and 22 on support legs 15 and 16 with rocker elements 41 and 42. As illustrated in FIGS. 1–3, the rocker elements 41 and 42 are simply affixed to support feet 21 and 22, respectively, so that when the space frame 12 is tilted toward the patient, the underside of the rocker elements 41 and 42 contact the underlying substrate 25. When the space frame 12 is pushed or otherwise returned to its original upright position, the rocker elements 41 and 42 no longer contact the substrate 25; instead, the support feet 21 and 22 do so. Through this design, the dressing-aid-and-transfer device 10 is stable when the patient is resting on the chest support 11. At the same time, the use of the rocker elements 41 and 42 provide the maximum lever arm in the transfer of the patient from the sitting to the prone position, thereby requiring minimal physical (or mechanical) effort in making that patient transfer. The prior transfer devices, on the other hand, either require greater effort in achieving such a transfer because the maximum lever arm is not used, or they do not provide for maximum stability after the transfer because the transfer device is not in its most stable position when the patient is positioned thereon. Commercially-available rockers, well known to those skilled in the art, may be used to form the rocker elements 41 and 42.

In order to make the patient transfer as easy as possible for a single individual acting as an attendant, the tops of support legs 17 and 18 are fitted with upper handles 43 and 44 of ergonomic design. In operation, the dressing-aid-and-transfer device 10 is positioned in close proximity to the seated patient, with the patient's legs located in the trapezoidal box 26. Using the upper handles 43 and 44, the attendant then pushes the space frame 12 toward the patient, using the rocker elements 41 and 42 on opposing support legs 15 and 16 as the pivoting means. The patient's arms are then draped over a top chest support surface 45 of the chest support 11. A supplemental securing device, such as a securing strap 46 may then be used to further stabilize the patient on the chest support 11. Next, the attendant pulls on the upper handles 43 and 44 to draw the patient out of a chair, etc. When the space frame 12 is in its stable position with all of the support feet 21-24 resting on the substrate 25, the patient's legs move out of the trapezoidal box 26, making removal of lower clothing much easier, as previously noted.

The upper handles 43 and 44 that extend beyond the upper chest support surface 45 effectively extend the length of the lever of the support legs 17 and 18 and therefore increase the leverage available to the attendant. As a result, a single attendant—one who can be much smaller than the patient—can effectively and easily pull that patient out of the seating position and on to the stable dressing-aid-and-transfer device 10 of the present invention. Of further importance in providing upper handles 43 and 44 that extend beyond the upper chest support surface 45 relates to the use of those handles as guides to direct the patient's upper body onto the chest support 11. In addition, the upper handles 43 and 44 act as lateral stabilizers once the patient is on the chest support 11 in that the patient is prevented from rolling off of the chest support 11 during any movement.

The dressing-aid-and-transfer device 10 of the present invention may also be utilized by the patient alone, provided that the patient has some mobility and strength. To that end, a lower handle 47 is affixed to back cross-piece 29 between support legs 17 and 18. The lower handle 47 is positioned so that when a patient is draped over the chest support 11 while the space frame 12 is tilted toward the seated patient, it is within the patient's reach. With little effort, and while grasping the lower handles 47, the patient can push himself or herself forward and thereby tip the space frame 12 back to its resting position. At that time, the patient is drawn out of the seated position. To further provide a patient with the independence associated with controlling the present invention, particularly a patient with very little strength and mobility, optional mechanical actuators 49 and 50 may be incorporated into the design of the space frame 12. By pushing one or more controller buttons located on the chest support 11 or on the space frame 12, the patient can effectively control the motion of the space frame 12.

Figure 5:
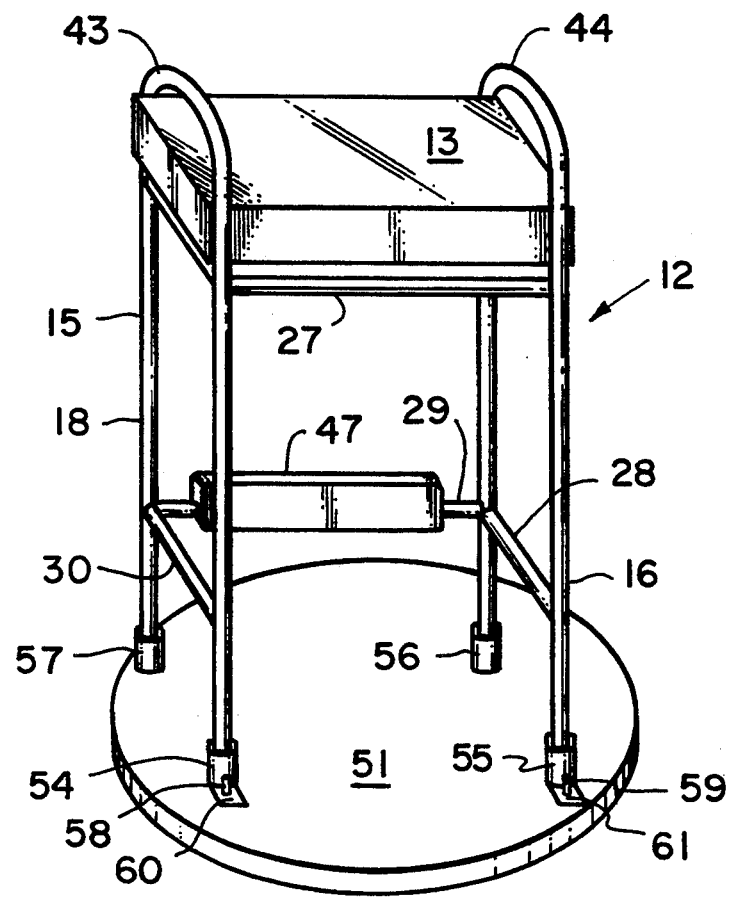
FIG. 5 is a simplified perspective view of the front of the present invention, showing the optional rotatable base.
Figure 6:
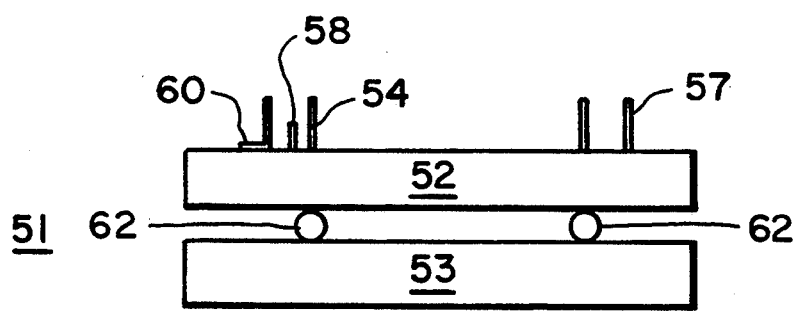
FIG. 6 is a simplified cross-sectional view of the rotatable base of the present invention.

The principal focus of the present invention is to provide a simple and effective means for one person to easily move an incapacitated patient from a seated to a stable prone position. It is also contemplated that an attendant, or the patient, should then be able to move that patient from one location to another. To that end, an optional rotatable base 51 is further provided, as illustrated in FIGS. 5 and 6. The rotatable base 51 of the present invention includes an upper base section 52 and a lower base section 53. While the rotatable base 51 may be a solid structure, it is contemplated that in keeping with the goal of a lightweight system, the rotatable base 51 is preferably a ring, as illustrated in the noted FIGS. The dressing-aid-and-transfer device 10 of the present invention is designed to rest on the upper base section 52, wherein support feet guides 54–57 act to secure said support feet 21–24 to said rotatable base 51. The support feet guides 54–57 are designed so that the support feet 21–24 may be removably inserted therein. Base guide hubs 58 and 59 act to lock support feet 21 and 22 in place in support feet guides 54 and 55 when the rotatable base 51 is to be used, while support feet 23 and 24 are permitted to move freely in and out of support feet guides 56 and 57 when the space frame 12 is tilted. Of course, it is to be understood that the support feet guides 54–57 can be designed differently; for example, they can be posts onto which the support feet 21–24 are placed and removably affixed. In either case, it is desirable that the support feet guides 54–57 are designed to provide for easy attachment or removal of the dressing-aid-and-transfer device 10 to the rotatable base 51.

When the rotatable base 51 is to be used, the rocker elements 41 and 42 may be replaced with pivoting means that are affixed to support feet guides 54 and 55. As illustrated in FIG. 5, hinges 60 and 61 are attached to support feet guides 54 and 55 so that when the space frame 12 is tilted, the rotatable base 51 remains completely on the substrate 25 while the space frame 12 operates as previously described. Of course, alternative pivoting means may be used, provided such means utilize the maximum possible lever arm.

In order to make the rotatable base 51 rotatable, there are roller elements 62, such as ball bearings, captured between the upper base section 52 and the lower base section 53. The lower base section 53 is in contact with the substrate 25 and has a suitable non-skid surface in contact with the substrate 25, thereby securing the rotatable base 51 in a single, stable position while the patient is being moved. The upper base section 52 is therefore free to rotate, as desired, on the roller elements 62. In effect, the upper base section 52, the roller elements 62, and the lower base section 53 act as a "lazy susan." This and other suitable rotational designs will be obvious to those skilled in the art, and alternatives, such as the use of wheels captured between the upper base section 52 and the lower base section 53, are also suitable.

While the dressing-aid-and-transfer device 10 and the rotatable base 51 of the present invention has been described and illustrated in detail herein, it will be apparent to those skilled in the art that substitutions, modifications, and equivalents of the materials and designed described herein may be made. For example, at least one horizontally-oriented supplemental handle may be affixed to the space frame 12 in close proximity to the chest support 11 and extending outwardly therefrom, so as to further reduce the effort required to lift the patient out of a chair.

Figure 7:
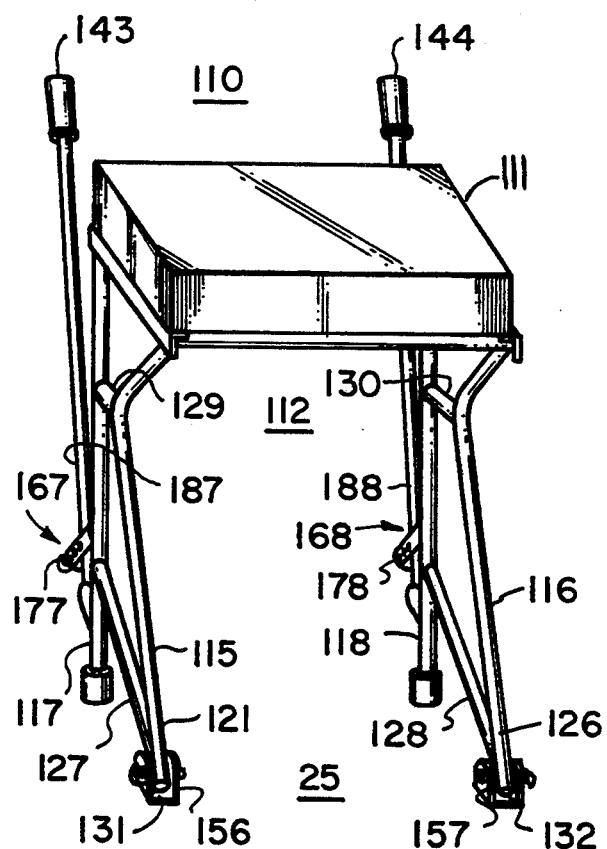
FIG. 7 is a simplified perspective view of an alternative design of the transfer device of the present invention, showing multi-position handles and the front support legs.
Figure 8:
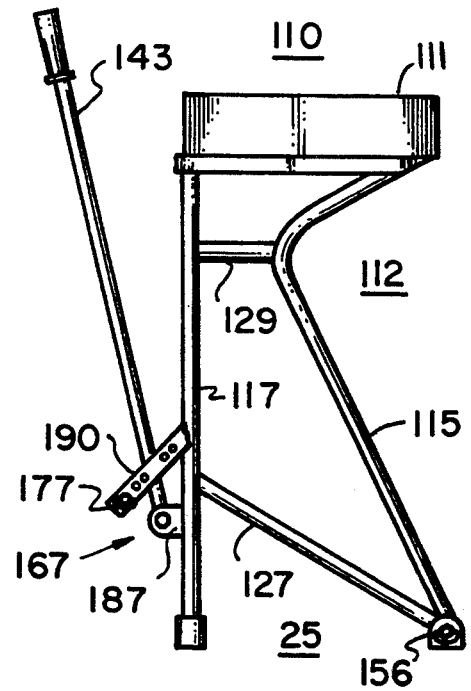
FIG. 8 is a simplified side elevation view of an alternative design of the transfer device of the present invention, showing different vertically-oriented support legs.

In an alternative embodiment of the present invention, illustrated in FIGS. 7 and 8, a second dressing-aid-and-transfer device 110 includes a space frame 112 having a plurality of essentially vertically-oriented support legs 115–118, and multiposition handles 143 and 144. The support legs 115–118 of the space frame 112 are configured to provide for stability of the device 110 while still permitting easy access to the patient's lower-body clothing without any interference. Front support legs 115 and 116 may be curved, at upper regions thereof, as illustrated in FIGS. 7 and 8, so as to minimize interference of those support legs with the patient's body. However, it is to be understood that other vertical support leg configurations may be used, such as the straight rear support legs 117 and 118 illustrated in the drawings, may also be used, provided they are designed to support the weight of any size patient during the transfer process. In this second preferred embodiment of the present invention, the support legs 115–118, as well as the multi-position handles 143 and 144, and cross-pieces 127–130 are made of Aluminum tubing. It is contemplated that other materials of sufficient strength, such as steel, high-strength plastics and the like may form some or all of the components of the present invention.

As with the first dressing-aid-and-transfer device 10 illustrated in the other drawings, the second dressing-aid-and-transfer device 110 includes pivot means located at front support feet 121 and 122 of front support legs 115 and 116. In this embodiment of the invention, the pivot means include support feet guides 156 and 157 to which the front support feet 121 and 122 are detachably affixed using removable support feet locking pins 131 and 132. The support feet guides 156 and 157 are designed to rest on an underlying substrate such as substrate 25. It is to be understood that a variety of pivoting means can be used, including, but not limited to the rocker elements 41 and 42 previously described, provided such pivoting means maintain the goal of the present invention to maximize the lever arm available to the attendant. Again, as with the other device 10 described, rear support feet 117 and 118 rest on the substrate 25 when the device 110 is in the upright position, while those same support legs are free to rise off the substrate 25 when the device 110 is pivoted toward the sitting patient.

The multi-position handles 143 and 144 enable the attendant to easily lift the patient from the sitting position to a position of being supported on a chest support 111 when the device 110 is in its upright position. When the handles 143 and 144 are in an upright position, they are essentially parallel with, and in close proximity to, the rear support legs 117 and 118. The handles 143 and 144 are preferably pivotally affixed to lower rear regions 167 and 168 of the rear support legs 117 and 118 so that they can optionally be pivoted through at least 90° from the vertical. Handle restrictor guides 177 and 178 on rear support legs 117 and 118 respectively, aid in fixing the handles 143 and 144 in a desired position. Handle restrictor pins 187 and 188, or other well-known means, may be used within a plurality of handle-position holes 190 of the restrictor guides 177 and 178 so as to lock the handles 143 and 144 in the desired position prior, or subsequent to, the patient transfer. It is contemplated that with the handles 143 and 144 in the farthest position from vertical, the device 110 may be used by a single attendant to transfer a patient from a position lying down on their back to a position on the device 110 with their chest supported by the chest support 111.

Figure 9:
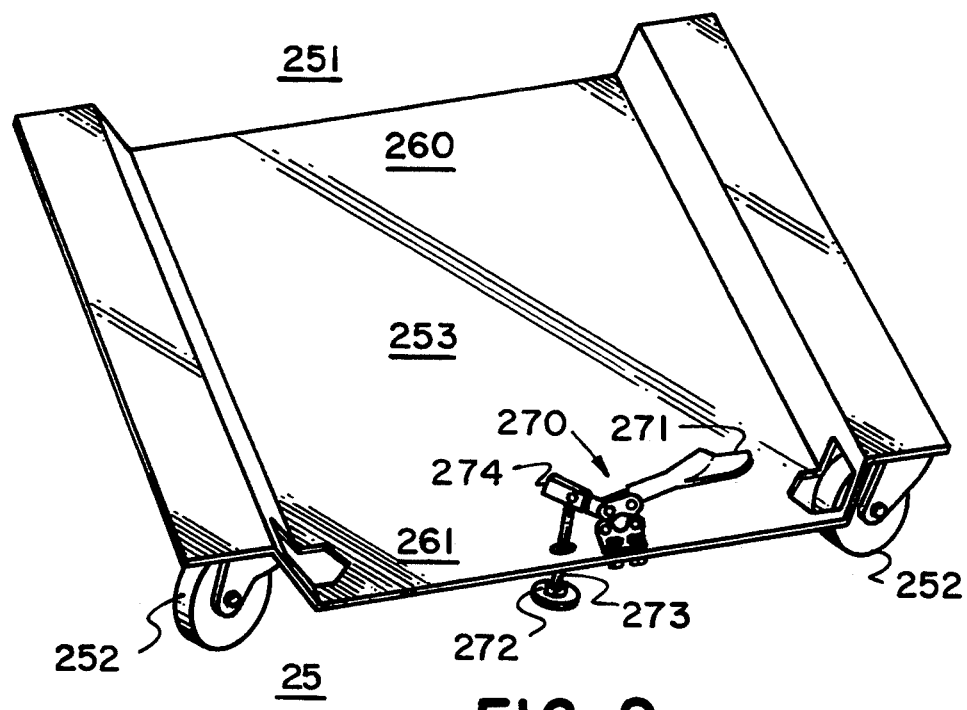
FIG. 9 is a simplified perspective view of a second optional rotatable base.

As illustrated in FIG. 9, a second optional rotatable base 251 may be included as a component of the device 110. The rotatable base 251 includes means for rotation, such as base wheels 252 swivably affixed to the underside of the base 251. For greatest stability, there are four base wheels 252 placed at the corners of the base 251. In addition to providing rotation of the base 251, the base wheels 252 also permit transfer of the patient from one location to the next. They also provide for easy transfer of the device 110 from one location to the next. While the base 251 may be planar, the preferred embodiment of the invention provides for a base trough 253 within which the space frame 112 is positioned. In that regard, the support feet guides 156 and 157 used to pivot the front support legs 115 and 116 are affixed to a front-base-trough section 260, with the rear support legs 117 and 118 resting on a rear-base-trough section 261. Whether the base 251 is planar or includes the base trough 253, it is contemplated that the patient's feet will rest thereon, with their chest supported by the chest support 111, for ease of delivery from one location to the next.

A device locking means is used to lock the device 110 in position when the patient is being transferred onto or off of the device 110. Such locking means may simply be well-known wheel locks associated with each of the base wheels 252 or, preferably, it may be a device stopper 270 as illustrated in FIG. 9. The device stopper 270 of the present invention may be affixed to the front-base-trough section 260 or, preferably, to the rear-base-trough section 261 for easy access by the attendant. The device stopper 270 includes an operating lever 271 that is pressed down to force a drag plate 272 into contact with the substrate 25 when it is desired to lock the device 110 in place during the transfer. The operating lever 271 also provides for release of the drag plate 272 when the device 110 is to be moved. The drag plate 272 may include a roughened underside for enhanced security, particularly when the substrate is a smooth surface. The drag plate 272 is linked to the operating lever 271 via a plate rod 273 and a hinge mechanism 274, all of which are of well-known design. It is to be understood that a variety of well-known stopping devices would achieve the same purpose sought for the operation of the optional base locking means.

The present embodiments described are illustrative and not restrictive. Therefore, all changes coming within the meaning and equivalency of the following claims are intended to be included therein.

I claim:

1. A device designed to aid in dressing and transferring an incapacitated patient, said device comprising:
   a. a space frame having a plurality of support legs defining a device perimeter;
   b. a horizontally-oriented substantially planar chest support connected to said space frame at an upper region thereof, wherein said chest support is adapted to support the chest of said patient; and
   c. pivot means connected to one or more of said support legs at lower ends thereof, said pivot means for pivoting said space frame from a vertical orientation toward said patient, wherein said patient is in a sitting position, and, upon placing the chest of said patient in contact with said chest support, for pivoting said space frame back to a vertical orientation with said patient supported on said chest support.

2. The device as claimed in claim 1 further comprising a plurality of cross-pieces connected to said support legs, wherein said cross-pieces are positioned so that the lower body of said patient, when in the process of transferring to or from a sitting position, is permitted to enter a space defined by said device perimeter.

3. The device as claimed in claim 2 wherein at least two of said cross-pieces are horizontally-oriented cross-pieces and said chest support is detachably connected to said horizontally-oriented cross-pieces.

4. The device as claimed in claim 1 further comprising a vertically-oriented handle connected to and extending from one of said support legs.

5. The device as claimed in claim 1 further comprising a plurality of vertically-oriented handles connected to and extending from a corresponding number of said plurality of support legs.

6. The device as claimed in claim 1 further comprising one or more horizontally-oriented handles connected to and extending from a middle region of one or more of said support legs.

7. The device as claimed in claim 1 wherein said pivot means are rocker mechanisms connected to said lower ends of two of said plurality of support legs such that when said space frame is tilted said rocker mechanisms contact an underlying substrate and when said space frame is in an upright position bottoms of said plurality of support legs contact said underlying substrate.

8. The device as claimed in claim 1 further comprising a safety strap connected to said chest support, wherein said safety strap acts to retain said patient on said chest support.

9. The device as claimed in claim 1 further comprising means to adjust the height of said chest support.

10. The device as claimed in claim 1 further comprising a rotatable base detachably connected to two or more of said plurality of support legs at lower ends thereof, wherein all of said plurality of support legs rest on said rotatable base.

11. The device as claimed in claim 10 wherein said pivot means comprise hinges connecting two or more of said plurality of support legs to said rotatable base, wherein said hinges are connected to those support legs in closest proximity to said patient.

12. The device as claimed in claim 10 further comprising locking wheels connected to an underside of said rotatable base, wherein said locking wheels contact an underlying substrate.

13. The device as claimed in claim 10 further comprising actuator means for automatically tilting said space frame.

14. The device as claimed in claim 1 further comprising actuator means for automatically tilting said space frame.

15. A device designed to aid in dressing and transferring a patient, said device comprising:
   a. a space frame having a front region and a rear region, two front support legs, two rear support legs, a first set of cross-pieces attached between said front and rear legs and a second set of cross-pieces attached between said front legs, said support legs defining an outer perimeter of said device;
   b. a horizontally-oriented substantially planar chest support connected to said cross-pieces wherein said chest support is adapted to support the chest of said patient;

c. a support platform attached to bottom ends of said rear support legs; and d. a plurality of pivoting mechanisms attached between bottom ends of said rear support legs and said support platform, wherein said space frame may be pivoted about said pivoting mechanisms from a vertical orientation toward said patient, wherein said patient is in a sitting position, and pivoted about said pivoting mechanisms back to a vertical orientation after the chest Of said patient has been placed on said chest support.

16. The device as claimed in claim 15, wherein said support platform is rotatable with respect to the underlying substrate on which said device rests.

17. The device as claimed in claim 15 further comprising a padded arm and hand support attached to said legs.

18. The device as claimed in claim 15 further comprising:

a. a safety strap for securing a person to said device while said person is resting against said chest support; and b. a plurality of body guides, said body guides attached to said space frame and extending above said chest support so as to keep a person positioned in the center of said chest support.

19. A device to aid in the dressing and transferring of a patient, said device comprising:

a. a space frame having four vertically-oriented support legs defining a device perimeter, and cross-pieces connecting said support legs together;

b. a horizontally-oriented substantially planar chest support connected to said support legs and to said cross-pieces at an upper region of said space frame, wherein said chest support is adapted to support the chest of said patient;

c. a rotatable base detachably connected to two of said Support legs at lower ends thereof and at a rear of said space frame, wherein said rotatable base is connected to said two rear support legs with hinges, wherein said hinges provide for the tilting of said space frame from a vertical orientation toward a sitting patient and back to a vertical orientation after placing the chest of said patient on said chest support so as to transfer said patient from a sitting position onto said device;

d. two vertically-oriented handles connected to and extending from two of said support legs at a front of said space frame;

e. two horizontally-oriented handles connected to middle regions of said two support legs at said front of said space frame;

f. a safety strap connected to said chest support, wherein said safety strap acts to retain said patient on said chest support;

g. means to adjust the height of said chest support; and h. actuator means for automatically tilting said space frame, 20. A device designed to aid in transferring an incapacitated patient, said device comprising:

a. a space frame having a plurality of support legs defining a device perimeter, wherein at least two of said support legs are substantially vertically-oriented;

b. a horizontally-oriented substantially planar chest support connected to said space frame at an upper region thereof, wherein said chest support is adapted to support the chest of said patient; and c. pivot means connected to one or more of said support legs at lower ends thereof, said pivot means for pivoting said space frame from a vertical orientation toward said patient, and, upon placing the chest of said patient in contact with said chest support, for pivoting said space frame back to a vertical orientation with said patient supported on said chest support.

21. The device as claimed in claim 20 further comprising one or more multiposition handles affixed to said space frame.

22. The device as claimed in claim 21 with said pivot means comprising locking pins pivotally connecting front support legs of said space frame to support leg guides.

23. The device as claimed in claim 22 further comprising a rotatable base detachably connected to said space frame.

24. The device as claimed in claim 23 wherein said rotatable base comprises a plurality of swivelable base wheels.

25. The device as claimed in claim 24 further comprising locking means for securing said device in position.

26. The device as claimed in claim 23 wherein said rotatable base includes a trough section within which said space frame is positioned.

* * * * *